United States Patent [19]
Nakamura et al.

[11] Patent Number: 4,568,768
[45] Date of Patent: Feb. 4, 1986

[54] PROCESS FOR PRODUCING M-HYDROXYACETOPHENONE

[75] Inventors: Makoto Nakamura, Ibaraki; Seiichi Kai; Nobuharu Kono, both of Toyonaka, all of Japan

[73] Assignee: Sumitomo Chemical Company, Limited, Osaka, Japan

[21] Appl. No.: 681,314

[22] Filed: Dec. 13, 1984

[30] Foreign Application Priority Data

Dec. 20, 1983 [JP]  Japan ................................ 58-241600

[51] Int. Cl.$^4$ ............................................. C07C 45/61
[52] U.S. Cl. ................................... 568/311; 568/309; 568/312; 568/322; 568/315
[58] Field of Search ............... 568/309, 311, 312, 322, 568/320, 315

[56] References Cited

U.S. PATENT DOCUMENTS 3,968,162  7/1976  Lartigau et al. .................... 568/311
4,113,779  9/1978  Bost et al. ........................... 568/311
4,486,605  12/1984  Harada et al. ...................... 568/311

FOREIGN PATENT DOCUMENTS 0084417  7/1983  European Pat. Off. ............ 568/311
21534  9/1965  Japan ................................... 568/311
28258  12/1965  Japan ................................... 568/311

Primary Examiner—Werren B. Lone
Attorney, Agent, or Firm—Stevens, Davis, Miller & Mosher

[57] ABSTRACT

A method for producing m-hydroxy-acetophenone which comprises allowing m-(2-hydroxy-2-propyl)cumene hydroperoxide to react at 30° to 100° C. in the presence of an aqueous solution containing 0.001 to 1 mole of iron salt per mole of said compound, 0.01 to 4 moles of copper salt per mole of said iron salt, and mineral acid to give m-(2-hydroxy-2-propyl)acetophenone, then allowing the resulting compound to react at 30° to 95° C. in the presence of 1 to 20 moles of 5 to 90% by weight aqueous hydrogen peroxide solution per mole of said compound and acid catalyst to form m-(2-hydroperoxy-2-propyl)acetophenone, and further subjecting the product formed to acid decomposition. m-Hydroxyacetophenone is an important intermediate in the fields of pharmaceuticals, agricultural chemicals, dyestuffs and the like.

23 Claims, No Drawings

PROCESS FOR PRODUCING M-HYDROXYACETOPHENONE

This invention relates to a process for producing m-hydroxyacetophenone.

m-Hydroxyacetophenone is an important intermediate in the fields of pharmaceuticals, agricultural chemicals, dyestuffs and the like. As the method for its production, there has been known a process which comprises, starting from acetophenone as the starting material, nitration, reduction, diazotization and hydrolysis.

However, the above process cannot be said to be industrially advantageous because it is relatively low in overall yield and involves too many reaction steps. Moreover, it has various defects in that it uses a large amount of strong acid and metal salt, thereby secondarily producing large amount of waste water and waste products and, in some cases, accompanying the evolution of poisonous gases.

In view of the circumstances, the present inventors have made extensive studies to develop a process for producing m-hydroxyacetophenone in a high overall yield and in an industrially advantageous way, and have resultantly attained the present invention.

Thus, according to this invention, there are provided a process for producing m-hydroxyacetophenone which comprises allowing m-(2-hydroxy-2-propyl) acetophenone to react at 30° to 95° C. in the presence of 1 to 20 moles of 5 to 90% by weight aqueous hydrogen peroxide solution per mole of said compound and acid catalyst to form m-(2-hydroperoxy-2-propyl)acetophenone and then subjecting the product formed to acid decomposition, as well as a process for producing m-hydroxyacetophenone which comprises the combination of the above-mentioned production process with a process for obtaining the starting compound of said process, m-(2-hydroxy-2-propyl) acetophenone, which comprises allowing m-(2-hydroxy-2-propyl)-cumene hydroperoxide to react at 30° to 100° C. in the presence of an aqueous solution containing 0.001 to 1 mole of iron salt per mole of said compound, 0.01 to 4 moles of copper salt per mole of said iron salt, and mineral acid.

Here, m-(2-hydroxy-2-propyl)cumene hydroperoxide (hereinafter referred to as CHPO.) may be easily obtained by the liquid phase air oxidation of m-diisopropylbenzene.

CHPO to be used in this invention should not necessarily be of high purity and may contain, for example, m-diacetylbenzene, m-acetylcumene, m-diisopropylbenzene, m-acetylcumene hydroperoxide and the like.

In the present invention, CHPO may be used as it is; but it is preferably used after dissolved in a suitable solvent for ease of operation. The organic solvents which may be used include aromatic hydrocarbons, ketones, ethers and aliphatic hydrocarbons and include, for example, benzene, toluene, xylene, cymene, methyl isobutyl ketone, n-butyl ether and n-hexane.

In the reaction of obtaining m-(2-hydroxy-2-propyl)acetophenone (hereinafter referred to as APCA) from CHPO, there is used as catalyst 0.001 to 1 mole of iron salt per 1 mole of CHPO and 0.01 to 4 moles of copper salt per 1 mole of the iron salt.

Examples of the iron salt include iron sulfate, iron chloride, iron nitrate, iron citrate, iron oxide such as ferric oxide, and iron hydroxide such as ferric hydroxide. Examples of the copper salt include copper sulfate, copper chloride, copper nitrate, copper acetate, copper oxide and copper hydroxide.

Also, together with these iron salt and copper salt, there is used 0.0005 to 0.1 mole of mineral acid, such as sulfuric acid, hydrochloric and nitric acid, per mole of CHPO. These are used in the form of an aqueous solution.

The aqueous solution containing iron salt, copper salt and acid mentioned above is usually used in an amount of 10 to 200 parts by weight relative to 100 parts by weight of the organic layer containing CHPO.

Amounts of iron salt, copper salt and acid used which are outside the above-mentioned ranges are unfavorable from the viewpoint of reaction rate, yield or economical efficiency.

The reaction is usually carried out at a temperature of 30° to 100° C. The end point of the reaction can be ascertained by the decrease in hydroperoxide group content in the reaction system. Usually, the reaction is carried out until the content of CHPO, the starting material, reaches 0.3% by weight or less based on the total reaction mixture.

Thus, APCA can be obtained in a high yield of 95 to 99% based on CHPO.

The reaction to obtain m-(2-hydroperoxy-2-propyl)acetophenone (hereinafter referred to as AHPO) from APCA is conducted at 30° to 95° C. in the presence of 1 to 20 moles of 5 to 90% by weight aqueous hydrogen peroxide solution per mole of APCA and acid catalyst.

Amounts of hydrogen peroxide used and its concentrations in the aqueous solution outside the above-mentioned ranges are unfavorable with respect to yield etc.

The APCA to be used in the reaction should not necessarily be of high purity and may contain or be contaminated with compounds which are inert to hydrogen peroxide.

Although APCA may be used as it is in the reaction, it is preferably used after dissolved in an organic solvent which is inert to hydrogen peroxide for ease of operation. Examples of such organic solvents include aromatic hydrocarbons such as benzene, toluene, xylene, cymene, halohydrocarbons such as dichloroethane, chlorobenzene, bromobenzene, ethers such as methoxybenzene, isopropyl ether, n-butyl ether and aliphatic hydrocarbons such as n-hexane. They are used each alone or in combination of two or more thereof.

As the acid catalyst, mineral acid such as sulfuric acid, hydrochloric acid, perchloric acid and phosphoric acid is used in a concentration of 0.05 to 10 moles per liter of aqueous hydrogen peroxide solution.

The reaction temperature is 30° to 95° C. The reaction pressure may be either atmospheric or reduced pressure. The water formed in the reaction may be distilled off during the course of the reaction.

The end point of the reaction can be ascertained by the conversion rate of APCA. Since too much amount of residual APCA causes not only decrease in the AHPO yield but also decrease in the yield of the subsequent step, acid decomposition of AHPO, the amount of remaining APCA is desirably reduced to a level as lower as possible. For example, the reaction should be carried out until the amount of remaining APCA reaches 0.2 mole or less relative to 1 mole of AHPO formed.

Thus, AHPO can be obtained in a high yield of 96 to 98% based on APCA.

The aqueous layer obtained after completion of the reaction may be recycled for further use.

The AHPO thus obtained is then subjected to acid decomposition.

The AHPO to be used in the acid decomposition should not necessarily be of high purity and may contain compounds which do not inhibit the acid decomposition. But since contamination with compounds having a carbinol group such as APCA and diisopropylbenzene carbinol causes decrease in decomposition yield, the amount of contaminating compounds having a carbinol group is preferably such that the amount of the carbinol group is 0.2 mole or less per 1 mole of AHPO.

In this reaction, AHPO is used, from the consideration for ease of operation and the like, after dissolved in an organic solvent which does not inhibit the acid decomposition.

Examples of such organic solvents include ketones such as methyl isobutyl ketone, acetone, aromatic hydrocarbons such as toluene, xylene, cymene and, in some cases, ethers, halohydrocarbons and aliphatic hydrocarbons. They are used each alone or in combination of two or more thereof.

In the reaction is used as acid catalyst sulfuric acid, hydrochloric acid, perchloric acid, boron trifluoride, sulfuric acid anhydride, toluenesulfonic acid or the like. Particularly preferred is sulfuric acid, perchloric acid, boron trifluoride or sulfuric acid anhydride. They are used preferably in an amount corresponding to an acid concentration of 5 to 10,000 ppm based on the total decomposition mixture. Use of too much acid causes coloration of the product and decrease in decomposition yield. Further, since too much moisture in the decomposition mixture hinders the smooth progress of the reaction, the water content in the total decomposition mixture is preferably 2% by weight or less.

The reaction temperature is usually 40° to 100° C. The reaction pressure may be either atmospheric or reduced pressure.

The reaction may be carried out while the acetone formed in the reaction and the solvent used are being distilled off.

The end point of the reaction can be ascertained by the conversion rate of AHPO. Generally, the reaction is finished when the content of remaining AHPO has reached 0.2% by weight or less based on the total decomposition mixture.

By means of such acid decomposition of AHPO, the intended m-hydroxyacetophenone (hereinafter referred to as OAO) can be obtained in a high yield of 96 to 99%.

The decomposition mixture obtained above may be treated by a conventional method such as extraction, acid precipitation, recrystallization, distillation or fractional distillation to give OAO of high purity.

This invention will be illustrated below with reference to Examples.

EXAMPLE 1

(1-a) Preparation of APCA from CHPO

Into a flask were placed 400 g of a methyl isobutyl ketone solution containing 20% by weight of CHPO (containing 0.53 mole of hydroperoxyde groups in the solution) and 200 g of an aqueous solution containing 0.01 mole of $FeSO_4$, 0.0053 mole of $CuSO_4$ and 0.0053 mole of sulfuric acid, and the mixture was reacted at 80° C. for 6 hours with stirring under $N_2$ atmosphere.

After completion of the reaction, the concentration of remaining hydroperoxide was found to be 0.2% by weight or less based on the total reaction mixture. The yield of APCA based on CHPO was 97.3%.

(1-b) Preparation of AHPO from APCA

From the methyl isobutyl ketone solution containing APCA obtained in (1-a) above, was removed methyl isobutyl ketone by distillation to give a cymene solution containing 65% by weight of APCA. Then, 101.5 g of the solution (containing 0.370 mole of APCA) was charged into a flask together with 3 moles of 60% by weight aqueous hydrogen peroxide solution based on 1 mole of APCA and 0.5% by weight of sulfuric acid based on the 60% by weight aqueous hydrogen peroxide solution. The mixture was allowed to react at 80° C. for 3 hours with stirring.

The conversion rate of APCA after the above reaction reached 98% or more. After cooled to room temperature, the organic layer was separated from the aqueous layer. The yield of AHPO based on APCA then was 96.8%.

(1-c) Preparation of OAO from AHPO

An 87 g of an acetone solution containing 0.04% by weight of $HClO_4$ was placed in a flask and brought up to 55° C. with stirring. To the solution was added dropwise 348 g of 20% by weight AHPO cymene solution (0.358 mole as AHPO) which had been prepared by removing water under reduced pressure from the reaction solution obtained in (1-b) above and adjusting the concentration of the resulting solution with cymene.

The temperature of the reaction mixture rose and the decomposition reaction took place. The dropwise addition of the AHPO cymene solution was further continued while the reaction mixture was being maintained at a temperature of 80° C. After completion of the addition, the mixture was kept at 80° C. for further 20 minutes. The residual content of hydroperoxide in the reaction solution after the above period was 0.1% by weight or less based on the total decomposition mixture. The decomposition yield of OAO formed was 97.4% based on OAO charged.

Overall yield in steps from (1-a) through (1-c) was 91.7%.

The cymene solution containing OAO obtained above was then stripped of acetone to give a cymene solution containing 15% by weight of OAO. The resulting OAO cymene solution (298 g, containing 0.328 mole of OAO) was treated with a 15% by weight aqueous NaOH solution (106 g, containing 0.397 mole of NaOH) to extract OAO into the aqueous layer. The aqueous layer was separated from the oil layer at 70° C. The alkaline layer obtained was acidified with 30% by weight aqueous sulfuric acid (50° C., pH=3.0), cooled down to 10° C., and the precipitated crystals were collected by filtration. The precipitated solid product thus obtained was distilled under vacuum to give a purified OAO; purity: 99.0% or higher, m.p.: 95.5° C.

The recovery of OAO through extraction, acid precipitation and distillation was 93.5%.

EXAMPLE 2

(2-a) Preparation of AHPO from APCA

A toluene solution containing 30% by weight of APCA (219.9 g solution, containing 0.370 mole of APCA), an amount of 20% by weight aqueous hydrogen peroxide solution corresponding to 5 equivalents per 1 equivalent of the APCA, and 1.0% by weight of sulfuric acid based on the weight of 20% by weight aqueous hydrogen peroxide solution were charged into a flask and the mixture was allowed to react with stirring at 70° C. for 5 hours. The conversion rate of APCA then was 98% or more and the yield of AHPO based on APCA was 97.6%.

The reaction mixture was cooled down to room temperature and then separated and isolated into organic layer and aqueous layer.

(2-b) Preparation of OAO from AHPO

An 87 g of methyl isobutyl ketone solution containing 0.04% by weight of $SO_3$ was placed in a flask, and brought to a temperature of 65° C. with stirring. To the solution was added dropwise 702 g of a 10% by weight of AHPO toluene solution (containing 0.361 mole of AHPO) which had been prepared by removing water from the reaction mixture obtained in (2-a) above by distillation under reduced pressure and then adjusting the concentration of the resulting solution with toluene.

The temperature of the reaction mixture rose and the decomposition reaction took place. The dropwise addition of the AHPO toluene solution was further continued while the reaction mixture was being maintained at a temperature of 70° C. After completion of the addition, the mixture was kept at 70° C. for further 20 minutes. The residual content of the hydroperoxide after the reaction was 0.1% by weight or less based on the total decomposition mixture. The yield in decomposition into OAO based on charged AHPO was 98.0%.

The resulting reaction solution was stripped of formed acetone by distillation to give a 10% by weight OAO toluene solution. Then, 482 g of the latter solution (containing 0.3538 mole of OAO) was treated with 106 g of 15% by weight aqueous NaOH solution (containing 0.397 mole of NaOH) to extract OAO into aqueous alkali. The aqueous layer was separated from the oil layer at 70° C. The alkaline layer obtained was acidified with 30% by weight aqueous sulfuric acid (50° C., pH=6.0), mixed with 300 g of methyl isobutyl ketone to extract OAO, and separated into aqueous and oil phases. The OAO methyl isobutyl ketone solution thus obtained was distilled under reduced pressure.

The resulting OAO had a purity of 99.0% or higher and a m.p. of 95.6° C. The recovery of OAO from the decomposition reaction solution was 94%.

EXAMPLE 3

(3-a) Preparation of APCA from CHPO

The preparation was conducted exactly in the same manner as in (1-a) of Example 1 except that 200 g of an aqueous solution containing 0.05 mole of $FeSO_4 \cdot 7H_2O$, 0.02 mole of $CuSO_4$ and 0.01 mole of sulfuric acid was used. The yield of APCA based on CHPO was 98.0%.

Successively, the APCA obtained above was converted into AHPO exactly in the same manner as in (1-b) of Example 1, and the resulting AHPO was converted exactly in the same manner as in (1-c) of Example 1 to obtain OAO.

What is claimed is:

1. A process for producing m-hydroxyacetophenone which comprises reacting m-(2-hydroxy-2-propyl)acetophenone with 1 to 20 moles of 5 to 90% by weight aqueous hydrogen peroxide solution per mole of said acetophenone at 30° to 95° C. in the presence of a mineral acid catalyst to form m-(2-hydroperoxy-2-propyl)acetophenone, and then decomposing the m-(2-hydroperoxy-2-propyl)acetophenone by warming with sulfuric acid, hydrochloric acid, perchloric acid, boron trifluoride, sulfuric acid anhydride or toluenesulfonic acid to form m-hydroxyacetophenone.

2. A process according to claim 1, wherein the reaction of m-(2-hydroxy-2-propyl)acetophenone with hydrogen peroxide is carried out in an organic solvent which is inert to hydrogen peroxide.

3. A process according to claim 2, wherein the organic solvent is an aromatic hydrocarbon, a halohydrocarbon, an ether, an aliphatic hydrocarbon or a mixture of two or more thereof.

4. A process according to claim 1, wherein the mineral acid is sulfuric acid, hydrochloric acid, perchloric acid or phosphoric acid.

5. A process according to claim 4, wherein the mineral acid is present in a concentration of 0.05 to 10 moles per liter of the aqueous hydrogen peroxide solution.

6. A process according to claim 1, wherein the m-(2-hydroperoxy-2-propyl)acetophenone is decomposed in an organic solvent which does not inhibit decomposition.

7. A process according to claim 6, wherein the organic solvent is a ketone, an aromatic hydrocarbon, an ether, a halohydrocarbon, an aliphatic hydrocarbon or a mixture of two or more thereof.

8. A process according to claim 1, wherein the m-2-hydroperoxy-2-propyl)acetophenone is decomposed in a mixture containing 5 to 10,000 ppm by weight of sulfuric acid, hydrochloric acid, perchloric acid, boron trifluoride, sulfuric acid anhydride or toluenesulfonic acid based on the total weight of the mixture.

9. A process according to claim 1, wherein decomposition is effected by warming at 40° to 100° C.

10. A process for preparing m-hydroxyacetophenone, which comprises heating m-(2-hydroxy-2-propyl)cumene hydroperoxide at 30° to 100° C. with an aqueous solution containing 0.001 to 1 mole of iron salt per mole of said hydroperoxide, 0.01 to 4 moles of copper salt per mole of said iron salt, and mineral acid to form m-(2-hydroxy-2-propyl)acetophenone, reacting m-(2-hydroxy-2-propyl)acetophenone with 1 to 20 moles of 5 to 90% by weight aqueous hydrogen peroxide solution per mole of said acetophenone at 30° to 95° C. in the presence of a mineral acid catalyst to form m-(2-hydroperoxy-2-propyl)acetophenone, and then decomposing the m-(2-hydroperoxy-2-propyl)acetophenone by warming with sulfuric acid, hydrochloric acid, perchloric acid, boron trifluoride, sulfuric acid anhydride or toluenesulfonic acid to form m-hydroxyacetophenone.

11. A process according to claim 10, wherein the reaction of m-(2-hydroxy-2-propyl)acetophenone with hydrogen peroxide is carried out in an organic solvent which is inert to hydrogen peroxide.

12. A process according to claim 11, wherein the organic solvent is an aromatic hydrocarbon, a halohydrocarbon, an ether, an aliphatic hydrocarbon or a mixture of two or more thereof.

13. A process according to claim 10, wherein the mineral acid is sulfuric acid, hydrochloric acid, perchloric acid or phosphoric acid.

14. A process according to claim 13, wherein the mineral acid is present in a concentration of 0.05 to 10 moles per liter of the aqueous hydrogen peroxide solution.

15. A process according to claim 10, wherein the m-(2-hydroperoxy-2-propyl)acetophenone is decomposed in an organic solvent which does not inhibit decomposition.

16. A process according to claim 15, wherein the organic solvent is a ketone, an aromatic hydrocarbon, an ether, a halohydrocarbon, an aliphatic hydrocarbon or a mixture of two or more thereof.

17. A process according to claim 10, wherein the m-(2-hydroperoxy-2-propyl)acetophenone is decomposed in a mixture containing 5 to 10,000 ppm by weight of sulfuric acid, hydrochloric acid, perchloric acid, boron trifluoride, sulfuric acid anhydride or toluenesulfonic acid based on the total weight of the mixture.

18. A process according to claim 10, wherein decomposition is effected by warming at 40° to 100° C.

19. A process according to claim 10, wherein the heating of m-(2-hydroxy-2-propyl)cumene hydroperoxide is carried out in an organic solvent.

20. A process according to claim 19, wherein the organic solvent is an aromatic hydrocarbon, a ketone, an ether, an aliphatic hydrocarbon or a mixture of two or more thereof.

21. A process according to claim 10, wherein the iron salt is iron sulfate, iron chloride, iron nitrate, iron citrate, iron oxide or iron hydroxide.

22. A process according to claim 10, wherein the copper salt is copper sulfate, copper chloride, copper nitrate, copper acetate, copper oxide or copper hydroxide.

23. A process according to claim 10, wherein the aqueous solution contains 0.005 to 0.1 mole of sulfuric acid, hydrochloric acid or nitric acid per mole of m-(2-hydroxy-2-propyl)cumene hydroperoxide.

* * * * *